(12) United States Patent
Lenz

(10) Patent No.: US 7,807,364 B2
(45) Date of Patent: Oct. 5, 2010

US007807364B2

(54) ANGIOGENESIS PATHWAY GENE POLYMORPHISMS FOR THERAPY SELECTION

(75) Inventor: Heinz-Josef Lenz, Altadena, CA (US)

(73) Assignee: University of Southern California, Los Angeles, CA (US)

( * ) Notice: Subject to any disclaimer, the term of this patent is extended or adjusted under 35 U.S.C. 154(b) by 443 days.

(21) Appl. No.: 11/681,695

(22) Filed: Mar. 2, 2007

(65) Prior Publication Data

US 2007/0207486 A1 Sep. 6, 2007

Related U.S. Application Data

(60) Provisional application No. 60/779,018, filed on Mar. 3, 2006.

(51) Int. Cl.
 C12Q 1/68 (2006.01)
 C12P 19/34 (2006.01)
 C07H 21/02 (2006.01)
 C07H 21/04 (2006.01)

(52) U.S. Cl. .......... 435/6; 435/91.2; 536/23.5; 536/24.31; 436/63; 436/64

(58) Field of Classification Search .......... None
See application file for complete search history.

(56) References Cited

U.S. PATENT DOCUMENTS

| | | | |
|---|---|---|---|
| 6,716,581 | B2 | 4/2004 | Lenz et al. |
| 2004/0011625 | A1 | 2/2004 | Lenz |
| 2004/0067519 | A1 | 4/2004 | Lenz et al. |
| 2006/0094012 | A1 | 5/2006 | Lenz et al. |
| 2006/0115827 | A1 | 6/2006 | Lenz |
| 2007/0218487 | A1 | 9/2007 | Lenz |
| 2007/0244083 | A1 | 10/2007 | Lenz |
| 2008/0286789 | A1 | 11/2008 | Lenz et al. |
| 2009/0181016 | A1 | 7/2009 | Lenz |

FOREIGN PATENT DOCUMENTS

WO  WO 2004/011625  2/2004

OTHER PUBLICATIONS

Erichsen et al. (Br J. Cancer, 2004, vol. 90, pp. 747-751).*
Hirshhorn et al. (Genetics in Medicine, 2002, 4(2): 45-61).*
Balasubramanian et al. (2002) "Role of genetic polymorphisms in tumour angiogenesis" *Br. J. Cancer* 87(10):1057-1065.
Ban et al. (1996) "Transfection of glutathione 5-transferase (GST)-pi antisense complementary DNA increases the sensitivity of a colon cancer cell line to adriamycin, cisplatin, melphalan, and etoposide" *Cancer Res.* 56(15):3577-3582.
Bello et al. (2006) "Analysis of circulating biomarkers of sunitinib malate in patients with unresectable neuroendocrine tumors (NET): VEGF, IL-8, and soluble VEGF receptors 2 and 3" *Proc ASCO* 24:4045.
Du Manoir et al. (2006) "Strategies for delaying or treating in vivo acquired resistance to Trastuzumab in human breast cancer xenografts," *Clin. Cancer Res.* 12:904-916.
Eberhart et al. (1994) "Up-regulation of cyclooxygenase 2 gene expression in human colorectal adenomas and adenocarcinomas" *Gastroenterology* 107(4):1183-1188.
Edelman (1988) "Morphoregulatory molecules" *Biochem.* 27(10):3533-3543.
Evans and Relling (1999) "Pharmacogenomics: translating functional genomics into rational therapeutics" *Science* 286(5439):487-491.
Folkman (2002) "Role of angiogenesis in tumor growth and metastasis" *Semin. Oncol.* 29(6 Suppl 16):15-18.
Gorski et al. (1999) "Blockage of the vascular endothelial growth factor stress response increases the antitumor effects of ionizing radiation" *Cancer Res.* 59(14):3374-3378.
Goto et al. (1999) "Overexpression of glutathione S-transferase pi enhances the adduct formation of cisplatin with glutathione in human cancer cells" *Free Rad. Res.* 31(6):549-558.
Iqbal et al. (2003) "Targeted therapy and pharmacogenomic programs," *Cancer* 97:2076-2082.
Kastan et al. (1991) "Participation of p53 protein in the cellular response to DNA damage" *Cancer Res.* 51(23 Pt 1):6304-6311.
Lenz (2004) "The use and development of germline polymorphisms in clinical oncology" *J. Clin. Oncol.* 22(13):2519-2521.
Lenz (2006) "Pharmacogenomics and colorectal cancer" *Adv. Exp. Med. Biol.* 587:211-231.
Levine (1992) "The p53 tumor-suppressor gene" *N. Engl. J. Med.* 326(20):1350-1352.
Levine et al. (2004) "Phase I trial of anti-sense oligonucleotide vascular endothelial growth factor (VEGF-AS, Veglin) in patients with relapsed and refractory malignancies" *Proc ASCO* 23:3008.
Mallik et al. (2004) "Polymorphisms in IL-8 and the GSTP1 are associated with survival of metastatic colorectal cancer patients treated with CPT-11" *Proc ASCO* 23:3606.
Mauceri et al. (1996) "Tumor necrosis factor alpha (TNF-alpha) gene therapy targeted by ionizing radiation selectively damages tumor vasculature" *Cancer Res.* 56(19):4311-4314.
Mauceri et al. (1998) "Combined effects of angiostatin and ionizing radiation in antitumour therapy" *Nature* 394(6690):287-291.
Maurer et al. (1998) "Over-expression of ICAM-1, VCAM-1 and ELAM-1 might influence tumor progression in colorectal cancer" *Int. J. Cancer* 79(1):76-81.
Miller et al. (2005) "Randomized phase III trial of capecitabine compared with Bevacizumab plus capecitabine in patients with previously treated metastatic breast cancer," *Journal of Clinical Oncology* 23:792-799.
Nunez et al. (1996) "Relationship between DNA damage, rejoining and cell killing by radiation in mammalian cells" *Radiother. Onc.* 39(2):155-165.

(Continued)

Primary Examiner—Sarae Bausch
(74) Attorney, Agent, or Firm—Antoinette F. Konski; Foley & Lardner LLP

(57) ABSTRACT

A method for determining whether a patient in need thereof will respond to anti-VEGF antibody based chemotherapy by screening a suitable cell or tissue sample isolated from the patient for at least one genomic polymorphism or genotype selected from (i) IL-8(−251); (ii) VEGF(936); or (iii) AM (3' CA repeats), wherein the patient is suitably treated if the corresponding genotype is (i) (T/T) for IL-8(−251); (ii) (T/T or C/T) for VEGF(936); or (iii) at least one AM allele having 14 or more 3' CA repeats.

15 Claims, No Drawings

OTHER PUBLICATIONS

Park and Lenz (2006) "Determinants of chemosensitivity in gastric cancer" *Curr. Opin. Pharma.* 6(4):337-344.

Ruoslahti (1988) "Fibronectin and its receptors" *Ann. Rev. Biochem.* 57:375-413.

Stoehlmacher et al. (2002) "Association between glutathione S-transferase P1, T1, and M1 genetic polymorphism and survival of patients with metastatic colorectal cancer" *J. Nat. Cancer Inst.* 94(12):936-942.

Wachsberger et al. (2003) "Tumor response to ionizing radiation combined with antiangiogenesis or vascular targeting agents: exploring mechanisms of interaction" *Clin. Cancer Res.* 9(6):1957-1971.

Yan and Beckman (2005) "Pharmacogenetics and pharmacogenomics in oncology therapeutic antibody development" *Biotechniqes* 39(4):565-568.

Yanagisawa et al. (1998) "Increased expression of human DNA repair genes, XRCC1, XRCC3 and RAD51, in radioresistant human KB carcinoma cell line N10" *Oral Oncol.* 34(6):524-528.

Yang et al. (2004) "Gene expressions of VEGF and Survivin as molecular markers of lymph node involvement in patients with locally advanced rectal cancer" *Proc ASCO* 23:9526.

Yuan et al. (2000) "Interleukin-8 messenger ribonucleic acid expression correlates with tumor progression, tumor angiogenesis, patient survival, and timing of relapse in non-small-cell lung cancer" *Am. J. Respir. Crit. Care Med.* 162(5):1957-163.

Yun et al. (2003) "Association of genetic polymorphisms of IL-8 and its receptor CXCR1 and survival of patients with metastatic colorectal cancer treated with 5FU/oxaliplatin" *Proc ASCO* 22:847.

Zhang et al. (2003) "Interleukin-8 (IL-8) promoter region gene polymorphism predicts pelvic recurrence after chemo-radiation in patients with rectal cancer" *Int. J. Radiat. Oncol. Riol. Phys.* 57(2):S382.

Zhang et al. (2006) "Cyclin D1 and epidermal growth factor polymorphisms associated with survival in patients with advanced colorectal cancer treated with Cetuximab" *Pharma. Genomics* 16(7):475-483.

Azuma et al. (2007) "Molecular markers associated with response and clinical outcome to cetuximab/bevacizumab/irinotecan (CBI) versus cetuximab/bevacizumab (CB) in irinotecan-refractory colorectal cancer (BOND2)" *J. Clin. Oncol., ASCO Ann. Mtg. Proc. I*, vol. 25(18S)(Jun. 20 Suppl):4113.

Chang et al. (2007) "Gene expression levels of HER2 and IL-8 and polymorphisms in IL-8 associated with clinical outcome in advanced or metastatic gastric cancer treated with lapatinib in SWOG 0413 trial," *J. Clin. Oncol., ASCO Ann. Mtg. Proc. I*, vol. 25(18S)(Jun. 20 Suppl):4647.

Fox, et al. (1998) "Angiogenesis in Normal Tissue Adjacent to Colon Cancer," *Journal of Surgical Oncology* 69(4):230-234.

Ishimitsu, et al. (2003) "Variations of human adrenomedullin gene and its relation to cardiovascular diseases," *Hypertension Research* 26(1):129-134.

Jin, et al. (2005) "Vascular endothelial growth factor polymorphisms in relations to breast cancer development and prognosis," *Clinical Cancer Research* 11(10)3647-3653.

Kuniyasu, et al. (2000) "Induction of Angiogenesis by Hyperplastic Colonic Mucosa Adjacent to Colon Cancer," *American Journal of Pathology* 157(5):1523-35.

Ladner et al. (2007) "Polymorphisms in estrogen receptor beta, interleukin-8, and interleukin-8 receptor associated with clinical outcome in metastatic colorectal cancer (mCRC) patients treated with 5-flourouracil/oxaliplatin," *J. Clin. Oncol., ASCO Ann. Mtg. Proc. I*, vol. 25(18S)(Jun. 20 Suppl):4130.

Lenz et al. (2006) "EGFR-Targeted Therapies in Solid Tumors," http://www.CancerPublications.com/.

Lenz et al. "Pharmacogenomic analysis of a randomized phase II trial (BOND 2) of cetuximab/bevacizumab/irinotacan (CBI) versus cetuximab/bevacizumab (CB) in irinotecan-refractory colorectal cancer," Presented at: *ASCO GI poster session*, 401. Orlando, FL. Jan. 21, 2007.

Liotta, et al. (2001) "The microenvironment of the tumour-host interface," *Nature* 411:375-79.

Loktionov (2004) "Common gene polymorphisms, cancer progression and prognosis," *Cancer Letters* 208:1-33.

Manegold et al. (2008) "ICAM-1, GRP-78, and FkB gene polymorphisms and clinical outcome in patients (pts) with metastatic colorectal cancer (mCRC) treated with first line 5-FU or capecitabine in combination with oxaliplatin and bevacizumab (FOLFOX/BV or XELOX/BV)," *Journal of Clinical Oncology*(15S):4134.

Pander, et al. (2007) "Pharmacogenetics of EGFR and VEGF Inhibition," *Drug Discovery Today* 12(23/24): 1054-60.

Schultheis et al. (2006) "Angiogenesis pathway gene polymorphisms associated with clinical outcome in recurrent ovarian cancer treated with low dose cyclophosphamide and bevacizumab: A California Consortium Trial," *J. Clin. Oncol., ASCO Ann. Mtg. Proc. I*, vol. 24(18S)(Jun. 20 Suppl):5017.

Schultheis et al. (2008) "Polymorphisms and Clinical Outcome in Recurrent Ovarian Cancer Treated with Cyclophosphamide and Bevacizumab," *Clin. Cancer Res.* 14(22):7554-7563.

Shaye, et al. (2007) "Polymorphisms in angiogenesis related genes predict clinical outcome in patients (pts) with metastatic colorectal cancer (mCRC) treated with first line 5-FU or capecitabine in combination with oxaliplatin and bevacizumab (FOLFOX/BV or XELOX/BV)," *J. Clin. Oncol., ASCO Ann. Mtg. Proc. I*, vol. 25(18S)(Jun. 20 Suppl):10576.

Smith, et al. (2004) "Cytokine gene polymorphisms and breast cancer susceptibility and prognosis," *European Journal of Immunogenetics* 31(4):167-173.

Stoeltzing, et al. (2003) "New Approaches to the Treatment of Hepatic Malignancies Angiogenesis and Antiangiogenic Therapy of Colon Cancer Liver Metastasis," *Annals of Surgical Oncology* 10(7):722-733.

Vallbohmer, et al. (2005) "Molecular Determinants of Cetuximab Efficacy," *Journal of Clinical Oncology* 23(15):3536-44.

Zhang et al. (2005) "Genomic polymorphisms of angiogenesis pathway predict radiosensitivity in rectal cancer," *Int. J. Radiation* 63:S284.

Zhang, et al. (2005) "Gene Polymorphisms of Epiderman Growth Factor Receptor and its Downstream Effector, Interleukin-8, Predict Oxaliplatin Efficacy in Patients with Advanced Colorectal Cancer," *Clinical Colorectal Cancer* 5(2):124-131.

Zhang et al. (2007) "Pharmacogenomic analysis of a randomized phase II trial (BOND 2) of cetuximab/bevacizumab/irinotecan (CBI) versus cetuximab/bevacizumab (CB) in irinotecan-refractory colorectal cancer," *J. Clin. Oncol., ASCO Ann. Mtg. Proc. I*, vol. 25(18S)(Jun. 20 Suppl):4128.

\* cited by examiner

ANGIOGENESIS PATHWAY GENE POLYMORPHISMS FOR THERAPY SELECTION

CROSS-REFERENCE TO RELATED APPLICATIONS

This application claims priority under 35 U.S.C. § 119(e) to provisional application No. 60/779,018, filed Mar. 3, 2006, the contents of which are incorporated by reference into the present disclosure.

STATEMENT OF GOVERNMENT SUPPORT

This invention was made with Government support under Contract No. CA082754 awarded by the National Institutes of Health. The U.S. Government has certain rights in the invention.

FIELD OF THE INVENTION

This invention relates to the field of pharmacogenomics and specifically to the application of genetic polymorphisms to diagnose and treat diseases.

BACKGROUND OF THE INVENTION

In nature, organisms of the same species usually differ from each other in some aspects, e.g., their appearance. The differences are genetically determined and are referred to as polymorphism. Genetic polymorphism is the occurrence in a population of two or more genetically determined alternative phenotypes due to different alleles. Polymorphism can be observed at the level of the whole individual (phenotype), in variant forms of proteins and blood group substances (biochemical polymorphism), morphological features of chromosomes (chromosomal polymorphism) or at the level of DNA in differences of nucleotides (DNA polymorphism).

Polymorphism also plays a role in determining differences in an individual's response to drugs. Cancer chemotherapy is limited by the predisposition of specific populations to drug toxicity or poor drug response. Thus, for example, pharmacogenetics (the effect of genetic differences on drug response) has been applied in cancer chemotherapy to understand the significant inter-individual variations in responses and toxicities to the administration of anti-cancer drugs, which may be due to genetic alterations in drug metabolizing enzymes or receptor expression. For a review of the use of germline polymorphisms in clinical oncology, see Lenz, H.-J. (2004) J. Clin. Oncol. 22(13):2519-2521; Park, D.J. et al. (2006) Curr. Opin. Pharma. 6(4):337-344; Zhang, W. et al. (2006) Pharma. and Genomics 16(7):475-483 and U.S. Patent Publ. No. 2006/0115827. For a review of pharmacogenetics and pharmacogenomics in therapeutic antibody development for the treatment of cancer, see Yan and Beckman (2005) Biotechniques 39:565-568.

Polymorphism also has been linked to cancer susceptibility (oncogenes, tumor suppressor genes and genes of enzymes involved in metabolic pathways) of individuals. In patients younger than 35 years, several markers for increased cancer risk have been identified. For example, prostate specific antigen (PSA) is used for the early detection of prostate cancer in asymptomatic younger males. Cytochrome P450 1A1 and glutathione S-transferase MI genotypes influence the risk of developing prostate cancer in younger patients. Similarly, mutations in the tumor suppressor gene, p53, are associated with brain tumors in young adults.

Results from numerous studies suggest several genes may play a major role in the principal pathways of cancer progression and recurrence, and that the corresponding germ-line polymorphisms may lead to significant differences at transcriptional and/or translational levels.

Moreover, while adjuvant chemotherapy and radiation lead to a noticeable improvement in local control among those with rectal carcinoma, the choice of optimal therapy may be compromised by a wide inter-patient variability of treatment response and host toxicity. Since the rate of inactivation of the administered drug compound may establish its effectiveness in the tumor tissue, genomic variations on different cellular mechanisms that may modify therapy efficacy may influence efficacy. In addition, tumor microenvironment is a critical pathway in cancer progression. Elements of cancer progression controlled by tumor microenvironment genes include angiogenesis, inter-cellular adhesion, mitogenesis, and inflammation. Angiogenesis, which involves the formation of capillaries from preexisting vessels, has been characterized by a complex surge of events involving extensive interchange between cells, soluble factors (e.g. cytokines), and extracellular matrix (ECM) components (Balasubramanian (2002) Br. J. Cancer 87:1057). In addition to its fundamental role in reproduction, development, and wound repair, angiogenesis has been shown to be deregulated in cancer formation (Folkman (2002) Semin. Oncol. 29(6):15).

Improvement in the therapeutic ratio of radiation by targeting tumor cells via a combination of angiogenic blockades and radiotherapy have been implicated in recent studies (Gorski (1999) Cancer Res. 59:3374; Mauceri (1996) Cancer Res. 56:4311; and Mauceri (1998) Nature 394:287). However, the mechanisms by which tumor cells respond to radiation through these antiangiogenic/vascular agents are yet to be elucidated. Moreover, in light of the fact that oxygen is a potent radiosensitizer, cancer therapy through the combination of ionizing radiation and antiangiogenic/vascular targeting agents may seem counterintuitive since a reduction in tumor vasculature would be expected to decrease tumor blood perfusion and lower oxygen concentration in the tumor (Wachsberger (2003) Clin. Cancer Res. 9:1957).

The interleukin family is known to play an important role in the angiogenic process. Interleukin-8, an inflammatory cytokine with angiogenic potential, has been implicated in cancer progression in a variety of cancer types including colorectal carcinoma, glioblastoma, and melanoma (Yuan (2000) Am. J. Respir. Crit. Care Med. 162:1957). Inter-cellular adhesion plays a major role in both local invasion and metastasis. Cell adhesion molecules (CAMs), which are cell-surface glycoproteins that are crucial for cell-to-cell interactions, have been shown to directly control differentiation, and interruption of normal cell-to-cell contacts has been observed in neoplastic transformation and in metastasis (Edelman (1988) Biochem. 27:3533 and Ruoslahti (1988) Ann. Rev. Biochem. 57:375). Overexpression of ICAM-1 in colorectal cancers has been shown to favor the extravasation and trafficking of cytotoxic lymphocytes toward the neoplastic cells, leading to host defense (Maurer (1998) Int. J. Cancer (Pred. Oncol.) 79:76). A polymorphism in the gene coding for Cox-2 was also studied. Cox-2 is involved in prostaglandin synthesis, and stimulates inflammation and mitogenesis; it has been shown to be markedly overexpressed in colorectal adenomas and adenocarcinomas when compared to normal mucosa (Eberhart (1994) Gastro. 107:1183). Another family of genes playing a critical role in angiogenesis is the receptor tyrosine kinase family of fibroblast growth factor receptors. FGFRs are also involved in tumor growth and cell migration.

The complex pathways of the tumor microenvironment have become the focus of widespread investigation for their role in tumor progression.

Differences in drug metabolism, transport, signaling and cellular response pathways have been shown to collectively influence diversity in patients' reactions to therapy (Evans (1999) Science 286:487). Metabolism of chemotherapeutic agents and radiation-induced products of oxidative stress, therefore, may play a critical role in treatment response. The GST superfamily participates in the detoxification processes of platinum compounds (Ban (1996) Cancer Res. 56:3577 and Goto (1999) Free Rad. Res. 31:549), and was previously associated GSTP1 polymorphism with response to platinum-based chemotherapy (Stoehlmacher (2002) J. Nat. Cancer Inst. 94:936).

Cell cycle regulation provides the foundation for a critical balance between proliferation and cell death, which are important factors in cancer progression. For example, a tumor suppressor gene such as p53 grants the injured cell time to repair its damaged DNA by inducing cell cycle arrest before reinitiating replicative DNA synthesis and/or mitosis (Kastan (1991) Cancer Res. 51:6304). More importantly, when p53 is activated based on DNA damage or other activating factors, it can initiate downstream events leading to apoptosis (Levine (1992) N. Engl. J. Med. 326:1350). The advent of tumor recurrence after radiation therapy depends significantly on how the cell responds to the induced DNA damage; that is, increased p53 function should induce apoptosis in the irradiated cell and thereby prevent proliferation of cancerous cells, whereas decreased p53 function may decrease apoptotic rates.

Finally, DNA repair capacity contributes significantly to the cell's response to chemoradiation treatment (Yanagisawa (1998) Oral Oncol. 34:524). Patient variability in sensitivity to radiotherapy can be attributed to either the amount of damage induced upon radiation exposure or the cell's ability to tolerate and repair the damage (Nunez (1996) Rad. Once. 39:155). Irradiation can damage DNA directly, or indirectly via reactive oxygen species, and the cell has several pathways to repair DNA damage including double-stranded break repair (DSBR), nucleotide excision repair (NER), and base excision repair (BER). An increased ability to repair direct and indirect damage caused by radiation will inherently lower treatment capability and hence may lead to an increase in tumor recurrence.

DESCRIPTION OF THE EMBODIMENTS

This invention provides methods to detect polymorphisms that have been determined to be clinically relevant to cancers that have been successfully treated with anti-VEGF antibody treatments.

In one aspect, the method requires determining the presence or absence of at least one allelic variant of a predetermined gene selected from the group consisting of a polymorphism at nucleotide −251 in the interleukin 8 gene [IL-8(−251)], a polymorphism at nucleotide 936 of the vascular endothelial growth factor gene [VEGF(936)] and a polymorphism in the 3' end of the adrenomedullin gene [AM (3' CA repeat)]. In another aspect, it requires determining two or more of the above-noted polymorphic regions. In a further aspect, it requires identifying all three. The genes of interest are selected from those shown to be involved with colon, breast, lung or ovarian cancer.

The invention also provides the tools to execute the methods of this invention. In one aspect, the tools can include using nucleic acids encompassing the polymorphic region of interest or adjacent to the polymorphic region as probes or primers.

In one aspect, the sample to be tested is the actual tumor tissue. In another aspect the sample can be normal tissue isolated adjacent to the tumor. In yet a further aspect, the sample is normal tissue corresponding to the tumor tissue (e.g., normal ovarian tissue when the cancer is ovarian cancer). In a further aspect, the sample is any tissue of the patient, and can include peripheral blood lymphocytes.

In another aspect, the invention comprises administration of an appropriate therapy or combination therapy after identification of the clinical correlation of the polymorphism of interest.

In yet a further aspect, the invention provides a kit for amplifying and/or for determining the molecular structure of at least a portion of the gene of interest, comprising a probe or primer capable of detecting to the gene of interest and instructions for use. In one embodiment, the probe or primer is capable of detecting a polymorph in the gene of interest.

It will be appreciated by one of skill in the art that the embodiments summarized above may be used together in any suitable combination to generate additional embodiments not expressly recited above, and that such embodiments are considered to be part of the present invention.

MODES FOR CARRYING OUT THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook et al. MOLECULAR CLONING: A LABORATORY MANUAL, $2^{nd}$ edition (1989); CURRENT PROTOCOLS IN MOLECULAR BIOLOGY (F.M. Ausubel et al. eds. (1987)); the series METHODS IN ENZYMOLOGY (Academic Press, Inc., N.Y.); PCR: A PRACTICAL APPROACH (M. MacPherson et al. IRL Press at Oxford University Press (1991)); PCR 2: A PRACTICAL APPROACH (M.J. MacPherson, B.D. Hames and G.R. Taylor eds. (1995)); ANTIBODIES, A LABORATORY MANUAL (Harlow and Lane eds. (1988)); ANIMAL CELL CULTURE (R.I. Freshney ed. (1987)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); TRANSCRIPTION AND TRANSLATION (B. D. Hames & S.J. Higgins eds. (1984)): IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); IMMUNOCHEMICAL METHODS IN CELL AND MOLECULAR BIOLOGY (Mayer and Walker, eds., Academic Press, London (1987)); HANDBOOK OF EXPERIMENTAL IMMUNOLOGY, Volumes I-IV (D. M. Weir and C. C. Blackwell, eds. (1986)): MANIPULATING THE MOUSE EMBRYO (Cold Spring Harbor Laboratory Press, Cold Spring Harbor, N.Y. (1986)).

Definitions

As used herein, certain terms may have the following defined meanings. As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, the term "vector" refers to a nucleic acid molecule capable of transporting another nucleic acid to which it has been linked. One type of preferred vector is an episome, i.e., a nucleic acid capable of extrachromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

The term "allelic variant of a polymorphic region of the gene of interest" refers to a region of the gene of interest having one of a plurality of nucleotide sequences found in that region of the gene in other individuals.

The expression "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu, D. Y. et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "genotype" refers to the specific allelic composition of an entire cell or a certain gene, whereas the term "phenotype" refers to the detectable outward manifestations of a specific genotype.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "a homolog of a nucleic acid" refers to a nucleic acid having a nucleotide sequence having a certain degree of homology with the nucleotide stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to a patient sample refers to tissue, cells, genetic material and nucleic acids, such as DNA or RNA, separated from other cells or tissue or DNAs or RNAs, respectively, that are present in the natural source. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an'RNA, the terms "adenosine", "cytidine", "guanosine", and thymidine" are used. It is understood that if the nucleic acid is RNA, a nucleotide having a uracil base is uridine.

The terms "oligonucleotide" or "polynucleotide", or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

A "polymorphic gene" refers to a gene having at least one polymorphic region.

As used herein, the term "gene of interest" or "polymorphism of interest" intends those exemplified herein, e.g., VEGF(936), IL-8(−251) and AM (3' CA repeats).

The term "treating" as used herein is intended to encompass curing as well as ameliorating at least one symptom of the condition or disease. For example, in the case of cancer, treatment includes a reduction in cachexia, increase in survival time, elongation in time to tumor progression, reduction in tumor mass, reduction in tumor burden and/or a prolongation in time to tumor metastasis, each as measured by standards set by the National Cancer Institute and the U.S. Food and Drug Administration for the approval of new drugs. See Johnson et al. (2003) J. Clin. Oncol. 21(7):1404-1411.

A "response" shall mean a 50% reduction in tumor.

A "complete response" (CR) to a therapy defines patients with evaluable but non-measurable disease, whose tumor and all evidence of disease had disappeared.

A "partial response" (PR) to a therapy defines patients with anything less than complete response that were simply categorized as demonstrating partial response.

"Non-response" (NR) to a therapy defines patients whose evidence of disease has remained constant or has progressed.

"Time to tumor progression" is the time between treatment and initial response and the time when resistance to initial treatment or loss of treatment efficacy.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975)).

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the antibody or compound that is effective to achieve a serum level commensurate with the concentrations found to be effective in vitro. Determination of these parameters is well within the skill of the art. These considerations, as well as effective formulations and administration procedures are well known in the art and are described in standard textbooks. Consistent with this definition, as used herein, the term "therapeutically effective amount" is an amount sufficient to treat a the cancer.

The compositions and compounds can be administered by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule.

Despite advances in chemotherapy, ovarian cancer remains a major cause of cancer mortality worldwide. It has therefore become essential to identify novel therapeutic targets, such as angiogenesis, which is a complex process regulated by the delicate balance between various local pro-angiogenic and anti-angiogenic proteins. Bevacizumab is a monoclonal antibody that binds to VEGF, and has shown significant activity in colon, breast, lung and ovarian cancer. It is sold under the tradename Avastin (Genentech). The antibody targets VEGF, a protein made by cells that stimulates the production of new blood vessels. VEGF is structurally related to platelet-derived growth factor (PDGF). The gene is located on chromosome 6p12.

The key enzymes of the VEGF pathway are: Vascular Endothelial Growth Factor (VEGF), VEGF Receptor (VEGFR), Hypoxia Inducible Factor-I (HIF α and β- subunit), Neuropilin-1 (NRP), Interleukin-8 (IL-8), Adrenomedullin (AM) and Leptin. Unexpectedly, Applicant found that IL-8(−251) is a molecular marker for response to Bevacizumab based cancer therapy. Patients homozygous (T/T) at nucleotide −251 for the IL-8 gene in patient samples were more responsive to this therapy than patients heterozygous (A/T) or homozygous (A/A). In this study, responsiveness was measured as a 50% reduction in tumor. Patients with any T (T/T or C/T) at nucleotide 936 for the VEGF gene showed more than double time to tumor progression than patients that were (C/C) at the same locus. Patients carrying one AM allele with more than 14 CA repeats were better responders and patients with both AM 3' end alleles having 14 or more CA repeats had the longest time to progression. In a further aspect, the AM genotype contains one allele containing 14 3' CA repeats or alternatively, both alleles contain 14 3' CA repeats.

Thus, a method is described to identify patients in need thereof, suitably treated by Bevacizumab based chemotherapy by screening or assaying a suitable patient sample for a polymorphism that has been correlated by Applicant to positive therapeutic response or separately, to time to tumor progression. Although Bevacizumab was the antibody therapy that was administered to patients in this reported study, the results can be extrapolated to any therapy which includes an anti-VEGF antibody with the same or similar activity to Bevacizumab. Antibodies with the same or similar activity can be described as "biologically equivalent". Methods to make and identify such antibodies are described herein.

In one aspect, the anti-VEGF antibody binds to any region or epitope on VEGF. In an alternative embodiment, the antibody binds to the same epitope on VEGF as Bevacizumab. In a further aspect, the antibody is a variant or derivative of Bevacizumab of any of the above and can include function fragments, derivatives or such antibodies conjugated to other agents.

In addition, although the particular patient population was undergoing treatment for ovarian cancer, the method is useful for any cancer that is amendable to anti-VEGF based chemotherapy as defined above. Such patients include, but are not limited to colon cancer patients, breast cancer patients and lung cancer patients, in addition to the exemplified ovarian cancer patients.

Suitable patient samples include tumor samples, normal tissue corresponding to the tumor type, tissue adjacent to the tumor and peripheral blood lymphocytes.

In one aspect a method is described for determining whether a patient in need thereof will respond to anti-VEGF antibody based chemotherapy by screening a suitable cell or tissue sample isolated from said patient for at least one genomic polymorphism or genotype selected from (i) IL-8(−251); (ii) VEGF(936); or (iii) AM (3' CA repeats), wherein the patient is suitably treated if the corresponding genotype is (i) (T/T) for IL-8(−251); (ii) (T/T or C/T) for VEGF(936); or (iii) at least one allele having 14 or more CA repeats (AM 3'). Patients carrying one AM allele with more than 14 CA repeats were better responders and patients with both AM 3' end alleles having 14 or more CA repeats were the best response to the therapy. In a further aspect, the patient is selected and considered a candidate for therapy when his or her AM genotype contains one allele containing 14 3' CA repeats or alternatively, both alleles contain 14 3' CA repeats.

In one aspect, the anti-VEGF antibody based therapy comprises the administration of a Bevacizumab antibody or its biological equivalent. In a further aspect, the patient is a cancer patient suffering from ovarian cancer, lung cancer, breast cancer or colon cancer. In another aspect, the cancer treatment further comprises administration of an effective amount of cyclophosphamide, e.g., a very low dose of cyclophosphamide. Effective amounts vary with the patient, the cancer being treated and can be determined by the treating physician.

Further described is a method for selecting anti-VEGF antibody based chemotherapy for a patient in need thereof by screening a suitable cell or tissue sample isolated from said patient for at least one genomic polymorphism or genotype selected from (i) IL-8(−251); (ii) VEGF(936); or (iii) AM (3' CA repeats), wherein the therapy is selected if the patient's corresponding genotype is (i) (T/T) for IL-8(−251); (ii) (T/T or C/T) for VEGF(936); or (iii) and one or both alleles having 14 or more CA repeats (AM 3'). In one aspect the patient is positive for two of the three genotypes. In a further aspect, the patient is positive for IL-8 (−251) and VEGF (936) and has one AM allele with 14 or more (3') CA repeats. In yet a further aspect, the patient is positive for IL-8 (−251) and VEGF (936) and has two AM alleles with 14 or more (3') CA repeats.

In one aspect, the anti-VEGF antibody based therapy comprises the administration of an effective amount of Bevacizumab antibody or its biological equivalent. In a further aspect, the patient is a cancer patient suffering from a cancer of the group ovarian cancer, lung cancer, breast cancer and colon cancer. In a yet further aspect, the cancer treatment further comprises administration of an effective amount of cyclophosphamide, e.g., a very lose dose of cyclophosphamide. Effective amounts vary with the patient, the cancer being treated and can be determined by the treating physician.

In general, a therapy is considered to "treat" cancer if it provides one or more of the following treatment outcomes: reduce or delay recurrence of the cancer after the initial therapy (i.e., time to tumor progression; reduction in tumor mass; reduction in tumor burden; increase median survival time or a decrease in tumor metastases). The method is particularly suited to determining which patients will be responsive or experience a positive treatment outcome to a chemotherapeutic regimen involving administration of Bevacizumab based chemotherapy or an equivalent anti-VEGF antibody therapy.

In one embodiment, the chemotherapeutic regimen further comprises radiation therapy or other adjuvant chemotherapy such as administration of a low dose of cyclophoshamide.

In addition to selecting a treatment protocol for the patient in need thereof, the method enables a doctor: 1) to more effectively prescribe a drug that will address the molecular basis of the disease or condition; 2) to better determine the appropriate dosage of a particular drug and 3) to identify novel targets for drug development.

Identification of the polymorphism can be accomplished by molecular cloning of the specified allele and subsequent sequencing of that allele using techniques known in the art. Alternatively, the gene sequences can be amplified directly from a genomic DNA preparation from the tumor tissue using PCR, and the sequence composition is determined from the amplified product. As described more fully below, numerous methods are available for analyzing a subject's DNA for mutations at a given genetic locus such as the gene of interest.

The polymorphism of interest can be identified using the methods exemplified below or any other of the various methods known to those skilled in the art. Art known methods include without limitation DNA microarray technology that also has many varieties, e.g., DNA chip devices and systems high-density microarrays for high-throughput screening applications and lower-density microarrays. Methods for microarray fabrication are known in the art and include various inkjet and microjet deposition or spotting technologies and processes, in situ or on-chip photolithographic oligonucleotide synthesis processes, and electronic DNA probe addressing processes. The DNA microarray hybridization applications has been successfully applied in the areas of gene expression analysis and genotyping for point mutations, single nucleotide polymorphisms (SNPs), and short tandem repeats (STRs). Additional methods include interference RNA microarrays and combinations of microarrays and other methods such as laser capture microdisection (LCM), comparative genomic hybridization (CGH) and chromatin immunoprecipitation (ChiP). For a review of these technologies, see He et al. (2007) Adv. Exp. Med. Biol. 593:117-133 and Heller (2002) Annu. Rev. Biomed. Eng. 4:129-153.

Other art-known methods include, without limitation PCR, xMAP, invader assay, mass spectrometry, and pyrosequencing (Wang et al. (2007) 593:105-106). The patent literature also describes art known methods for SNP analysis.

A detection method is allele specific hybridization using probes overlapping the polymorphic site and having about 5, or alternatively 10, or alternatively 20, or alternatively 25, or alternatively 30 nucleotides around the polymorphic region. In another embodiment of the invention, several probes capable of hybridizing specifically to the allelic variant are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244.

In other detection methods, it is necessary to first amplify at least a portion of the gene of interest prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al., (1989) Proc. Natl. Acad. Sci. USA 86:1173-1177), Q-Beta Replicase (Lizardi, P. M. et al. (1988) Bio/Technology 6:1197), or any other nucleic acid amplification method, followed by the detection of the amplified molecules using techniques known to those of skill in the art. These detection schemes are useful for the detection of nucleic acid molecules if such molecules are present in very low numbers.

In one embodiment, any of a variety of sequencing reactions known in the art can be used to directly sequence at least a portion of the gene of interest and detect allelic variants, e.g., mutations, by comparing the sequence of the sample sequence with the corresponding wild-type (control) sequence. Exemplary sequencing reactions include those based on techniques developed by Maxam and Gilbert ((1997) Proc. Natl. Aced Sd, USA 74:560) or Sanger (Sanger et al. (1977) Proc. Nat. Acad. Sci, 74:5463). It is also contemplated that any of a variety of automated sequencing procedures can be utilized when performing the subject assays (Biotechniques (1995) 19:448), including sequencing by mass spectrometry (see, for example, U.S. Pat. No. 5,547,835 and International Patent Application Publication Number WO94/16101, entitled DNA Sequencing by Mass Spectrometry by H. Koster; U.S. Pat. No. 5,547,835 and international patent application Publication Number WO 94/21822 entitled "DNA Sequencing by Mass Spectrometry Via Exonuclease Degradation" by H. Koster; U.S. Pat. No. 5,605,798 and International Patent Application No. PCT/US96/03651 entitled DNA Diagnostics Based on Mass Spectrometry by H. Koster; Cohen et al. (1996) Adv. Chromat. 36:127-162; and Griffin et al. (1993) Appl. Biochem Bio. 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA Sequencing Employing A Mixed DNA-Polymer Chain Probe" and U.S. Pat. No. 5,571,676 entitled "Method For Mismatch-Directed In Vitro DNA Sequencing."

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249, Cotton et al. (1988) Proc. Natl. Acad. Sci. USA 85:4397; Saleeba et al. (1992) Methods Enzy. 217:286-295. In another embodiment, the control or sample nucleic acid is labeled for detection.

In other embodiments, alterations in electrophoretic mobility is used to identify the particular allelic variant. For example, single strand conformation polymorphism (SSCP) may be used to detect differences in electrophoretic mobility between mutant and wild type nucleic acids (Orita et al. (1989) Proc Natl. Acad. Sd USA 86:2766; Cotton (1993) Mutat. Res. 285:125-144 and Hayashi (1992) Genet Anal Tech Appl 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al. (1989) Proc. Natl. Acad. Sci USA 86:6230 and Wallace et al. (1979) Nucl. Acids Res. 6:3543). Such allele specific oligonucleotide hybridization techniques may be used for the detection of the nucleotide changes in the polymorphic region of the gene of interest. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238 and Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al. (1992) Mol. Cell Probes 6:1).

In another embodiment, identification of the allelic variant is carried out using an oligonucleotide ligation assay (OLA), as described, e.g., in U.S. Pat. No. 4,998,617 and in Laridegren, U. et al. Science 241:1077-1 080 (1988). The OLA protocol uses two oligonucleotides which are designed to be capable of hybridizing to abutting sequences of a single strand of a target. One of the oligonucleotides is linked to a separation marker, e.g., biotinylated, and the other is detectably labeled, If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. (U.S.A.) 87:8923-8927). In this method, PCR is used to achieve the exponential amplification of target DNA, which is then detected using OLA.

Several techniques based on this OLA method have been developed and can be used to detect the specific allelic variant of the polymorphic region of the gene of interest. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in To be et al. (1996) Nucleic Acids Res. 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting the single nucleotide polymorphism in the gene of interest. Because single nucleotide polymorphisms in the gene of interest. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of the polymorphic site (Cohen, D. et al. (French Patent 2,650,840; PCT Appln. No. WO 91/02087)). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). This method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. supra, is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al. (1989) Nucl. Acids. Res. 17:7779-7784; Sokolov, B. P. (1990) Nucl. Acids Res. 18:3671; Syvanen, A.-C., et al. (1990) Genomics 8:684-692; Kuppuswamy, M. N. et al. (1991) Proc. Natl. Acad. Sci. (U.S.A.) 88:1143-1147; Prezant, T. R. et al. (1992) Hum. Mutat. 1: 159-164; Ugozzoli, L. et al. (1992) GATA 9:107-112; Nyren, P. et al. (1993) Anal. Biochem. 208:171-175). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al. (1993) Amer. J. Hum. Genet. 52:46-59).

If the polymorphic region is located in the coding region of the gene of interest, yet other methods than those described above can be used for determining the identity of the allelic variant. For example, identification of the allelic variant, which encodes a mutated signal peptide, can be performed by using an antibody specifically recognizing the mutant protein in, e.g., immunohistochemistry or immunoprecipitation. Antibodies to the wild-type or signal peptide mutated forms of the signal peptide proteins can be prepared according to methods known in the art.

Moreover, it will be understood that any of the above methods for detecting alterations in a gene or gene product or polymorphic variants can be used to monitor the course of treatment or therapy.

The methods described herein may be performed, for example, by utilizing pre-packaged diagnostic kits, such as those described below, comprising at least one probe or primer nucleic acid described herein, which may be conveniently used, e.g., to determine whether a subject has or is at risk of developing disease such as colorectal cancer.

Sample nucleic acid for use in the above-described diagnostic and prognostic methods can be obtained from any cell type or tissue of a subject. For example, a subject's bodily fluid (e.g. blood) can be obtained by known techniques (e.g., venipuncture). Alternatively, nucleic acid tests can be performed on dry samples (e.g., hair or skin). Fetal nucleic acid samples can be obtained from maternal blood as described in International Patent Application No. WO91/07660 to Bianchi. Alternatively, amniocytes or chorionic villi can be obtained for performing prenatal testing.

Diagnostic procedures can also be performed in situ directly upon tissue sections (fixed and/or frozen) of patient tissue obtained from biopsies or resections, such that no nucleic acid purification is necessary. Nucleic acid reagents can be used as probes and/or primers for such in situ procedures for (see, for example, Nuovo, G. J. (1992) "PCR In Situ Hybridization: Protocols And Applications", Raven Press, NY).

In addition to methods which focus primarily on the detection of one nucleic acid sequence, profiles can also be assessed in such detection schemes. Fingerprint profiles can be generated, for example, by utilizing a differential display procedure, Northern analysis and/or RT-PCR.

The invention described herein relates to methods and compositions for determining and identifying the allele present at the gene of interest's locus. This information is useful to diagnose and prognose disease progression as well as select the most effective treatment among treatment options. Probes can be used to directly determine the genotype of the sample or can be used simultaneously with or subsequent to amplification. The term "probes" includes naturally occurring or recombinant single- or double-stranded nucleic acids or chemically synthesized nucleic acids. They may be labeled by nick translation, Klenow fill-in reaction, PCR or other methods known in the art. Probes of the present invention, their preparation and/or labeling are described in Sambrook et al. (1989) supra. A probe can be a polynucleotide of any length suitable for selective hybridization to a nucleic acid containing a polymorphic region of the invention. Length of the probe used will depend, in part, on the nature of the assay used and the hybridization conditions employed.

In one embodiment of the invention, probes are labeled with two fluorescent dye molecules to form so-called "molecular beacons" (Tyagi, S. and Kramer, F.R. (1996) Nat. Biotechnol. 14:303-8). Such molecular beacons signal binding to a complementary nucleic acid sequence through relief of intramolecular fluorescence quenching between dyes bound to opposing ends on an oligonucleotide probe. The use of molecular beacons for genotyping has been described (Kostrikis, L.G. (1998) Science 279:1228-9) as has the use of multiple beacons simultaneously (Marras, S.A. (1999) Genet. Anal. 14:151-6. A quenching molecule is useful with a particular fluorophore if it has sufficient spectral overlap to substantially inhibit fluorescence of the fluorophore when the two are held proximal to one another, such as in a molecular beacon, or when attached to the ends of an oligonucleotide probe from about 1 to about 25 nucleotides.

Labeled probes also can be used in conjunction with amplification of a polymorphism. (Holland et al. (1991) Proc. Natl. Acad. Sci. 88:7276-7280). U.S. Pat. No. 5,210,015 by Gelfand et al. describe fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "Taq-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The Taq-Man approach uses a probe containing a reporter molecule-quencher molecule pair that specifically anneals to a region of a target polynucleotide containing the polymorphism.

Probes can be affixed to surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayyem et al. U.S. Pat. No. 5,952,172 and by Kelley, S. O. et al. (1999) Nucleic Acids Res. 27:4830-4837.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564 and 5,256,775).

Methods of Treatment

The invention further provides methods of treating subjects having cancer after they have been identified as suitable for anti-VEGF based chemotherapy by administering an effective amount of an anti-VEGF antibody. In one embodiment, the method comprises (a) determining the identity of the allelic variant identified herein as relevant to sensitivity to VEGF-antibody based chemotherapy; and (b) administering to the subject an effective amount of an anti-VEGF antibody or an equivalent of the antibody.

The antibody administered to the patient can be an anti-VEGF monoclonal antibody, an anti-VEGF polyclonal antibody, an active fragment thereof or a derivative or a variant thereof. These compositions can be conjugated to additional diagnostic or therapeutic agents. They can be administered alone or in combination with other effective or experimental therapies. Antibodies with the same or similar affinity and biological activity to Bevacizumab are examples of such antibodies.

Typically, the antibodies for use in these methods are monoclonal antibodies, although in certain aspects, polyclonal antibodies can be utilized. They can be chimeric, humanized, or totally human. The antibodies can be produced in cell culture, in phage, or in various animals, including but not limited to cows, rabbits, goats, mice, rats, hamsters, guinea pigs, sheep, dogs, cats, monkeys, chimpanzees, apes, etc. So long as the fragment or derivative retains specificity of binding or neutralization ability as the antibodies of this invention it can be used. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsried/Planegg, Del.), Biovation (Aberdeen, Scotland, UK) Biolnvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al., (1996) Crit. Rev. Biotechnol. 16:95-118; Eren et al. (1998) lmmunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al., (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. lmmunol. 17:887-892; Babcook et al., Proc. Natl. Acad. Sci. USA (1996) 93:7843-7848); gel microdroplet and flow cytometry (Powell et al. (1990) Biotechnol. 8:333-337; One Cell Systems, (Cambridge, Mass).; Gray et al. (1995) J. Imm. Meth. 182:155-163; Kenny et al. (1995) Bio/Technol. 13:787-790); B-cell selection (Steenbakkers et al. (1994) Molec. Biol. Reports 19:125-134 (1994).

Antibody variants or biological equivalents thereof can also be prepared by delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbiol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., Adv. Exp. Med. Biol. (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to know methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies of the present invention can be performed using any known method, such as but not limited to those described in U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel, N. D. et al. (2000) Infection and Immunity April 2000:1820-1826; Gallo, M. L. et al. (2000) European J. of Immun. 30:534-540; Green, L. L. (1999) J. of Immun. Methods 231:11-23; Yang, X-D et al. (1999A) J. of Leukocyte Biology 66:401-410; Yang, X-D (1999B) Cancer Research 59(6):1236-1243; Jakobovits, A. (1998) Advanced Drug Delivery Reviews 31:33-42; Green, L. and Jakobovits, A. (1998) J. Exp. Med. 188(3):483-495; Jakobovits, A. (1998) Exp. Opin. Invest. Drugs 7(4):607-614; Tsuda, H. et al. (1997) Genomics 42:413-421; Sherman-Gold, R. (1997). Genetic Engineering News 17(14); Mendez, M. et al. (1997) Nature Genetics 15:146-156; Jakobovits; A. (1996) Weir's Handbook of Experimental Immunology, The Integrated Immune System Vol. IV, 194.1-194.7; Jakobovits, A. (1995) Current Opinion in Biotechnology 6:561-566; Mendez, M. et al. (1995) Genomics 26:294-307; Jakobovits, A. (1994) Current Biology 4(8):761-763; Arbones, M. et al. (1994) Immunity 1(4):247-260; Jakobovits, A. (1993) Nature 362(6417): 255-258; Jakobovits, A. et al. (1993) Proc. Natl. Acad. Sci. USA 90(6):2551-2555; Kucherlapati, et al. U.S. Pat. No. 6,075,181.)

Human monoclonal antibodies can also be produced by a hybridoma which includes a B cell obtained from a transgenic nonhuman animal, e.g., a transgenic mouse, having a genome comprising a human heavy chain transgene and a light chain transgene fused to an immortalized cell.

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

The term "antibody derivative" also includes "diabodies" which are small antibody fragments with two antigen-binding sites, wherein fragments comprise a heavy chain variable domain (SI) connected to a light chain variable domain (V) in the same polypeptide chain (VH V). (See for example, EP 404,097; WO 93/11161; and Hollinger et al., (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen.)

The term "antibody derivative" further includes "linear antibodies". The procedure for making the is known in the art and described in Zapata et al. (1995) Protein Eng. 8(10): 1057-1062. Briefly, these antibodies comprise a pair of tandem Fd segments (V-$C_1$-VH-Cl) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), bismuth-213 (213 Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restriction (a ribosome inactivating protein produced by *Aspergillus restrictus*), saporin (a ribosome inactivating protein from *Saponaria officinalis*), and RNase; tyrosine kinase inhibitors; 1y207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

Modified antibodies of the invention also can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis. See generally, Hermanson, G. T., BIOCONJUGATE TECHNIQUES, Academic Press: San Diego, Calif. (1996).

Kits

As set forth herein, the invention also provides diagnostic methods for determining the type of allelic variant of a polymorphic region present in the gene of interest or the expression level of a gene of interest. In some embodiments, the methods use probes or primers comprising nucleotide sequences which are complementary to the polymorphic region of the gene of interest. Accordingly, the invention provides kits for performing these methods.

In an embodiment, the invention provides a kit for determining whether a subject is likely to respond to anti-VEGF antibody based chemotherapy. The kits contain one of more of the compositions described above and instructions for use. As an example only, the invention also provides kits for determining response to cancer treatment containing a first and second oligonucleotide specific for the polymorphic region of the gene of interest, e.g., IL-8 (−251), VEGF(936) or AM (3' CA repeat). Oligonucleotides "specific for" a genetic locus bind either to the polymorphic region of the locus or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, and preferably less than 1 kb from the polymorphism. Specific oligonucleotides are capable of hybridizing to a sequence, and under suitable conditions will not bind to a sequence differing by a single nucleotide.

The kit can comprise at least one probe or primer which is capable of specifically hybridizing to the polymorphic region of the gene of interest and instructions for use. The kits preferably comprise at least one of the above described nucleic acids. Preferred kits for amplifying at least a portion of the gene of interest comprise two primers, at least one of which is capable of hybridizing to the allelic variant sequence. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In one embodiment, the preferred surface is silica or glass. In another embodiment, the surface is a metal electrode.

Yet other kits of the invention comprise at least one reagent necessary to perform the assay. For example, the kit can comprise an enzyme. Alternatively the kit can comprise a buffer or any other necessary reagent.

Conditions for incubating a nucleic acid probe with a test sample depend on the format employed in the assay, the detection methods used, and the type and nature of the nucleic acid probe used in the assay.

The kits can include all or some of the positive controls, negative controls, reagents, primers, sequencing markers, probes and antibodies described herein for determining the subject's genotype in the polymorphic region of the gene of interest.

As amenable, these suggested kit components may be packaged in a manner customary for use by those of skill in the art. For example, these suggested kit components may be provided in solution or as a liquid dispersion or the like.

The invention now being generally described, it will be more readily understood by reference to the following examples which are included merely for purposes of illustration of certain aspects and embodiments of the present invention, and are not intended to limit the invention.

Experimental Example

IL-8 also has been identified as being involved in the VEGF pathway. A common single nucleotide polymorphism was identified 251 base pairs upstream of the IL-8 transcription start site and the IL-8 (−251A) allele was found to be associated with increased IL-8 production.

The VEGF (C936T) gene polymorphism, located in the 3'-UTR of VEGF gene, has been associated with low VEGF plasma levels and reduced breast cancer risk.

Adrenomedullin (AM) is a hypotensive peptide widely produced in the cardiovascular organs and tissues such as the heart, kidney and vascular cells. The 3'-end of the gene is flanked by a microsatellite marker of cytosine adenine (CA) repeats. In Japanese, four types of alleles with different CA-repeat numbers are reported to exist: 11, 13, 14 and 19 (Ishimitsu, T et al. (2001) Peptides 22(11): 1739-1744). The DNA variation was reported not to affect transcription of the gene.

Study Design: Seventy (70) patients with refractory ovarian cancer were enrolled in a Phase II clinical trial and treated with very low dose cyclophosphamide (50 mg po in combination with Bevacizumab (10 mg/kg) IV every 14 days. Different gene polymorphisms of angiogenic factors (VEGF +936 C/T, IL-8 −251 AT, and AM 3' less than (<) 14 CA repeats) were examined using PCR-RFLP. Primers are identified below.

| Gene | Polymorph Location | Function | Forward Primer | SEQ ID NO: | Reverse Primer | SEQ ID NO: | Enzyme |
|---|---|---|---|---|---|---|---|
| VEGF936 | C/T 936 | reduced plasma levels for T allele | ACA CCA TCA CCA TCG ACA GA | 1 | TCG GTG ATT TAG CAG CAA GA | 2 | NIa III |
| IL8 | −251 A/T | variant higher levels of IL8 | TTG TTC TAA CAC CTG CCA CTC T | 3 | GGC AAA CCT GAG TCA TCA CA | 4 | Mfe I |
| AM | 3'end CA repeat | associated with Hypertension | AAG AGG CTG AGT CAG AAG GAT TGG | 5 | GCA ACA TCA TTT TAA TAT CCT GCA CAG | 6 | |

Results: Thirteen (13) patients had a partial response (PR (256%)) and 39 were non responders (NR). Thirty-one patients had progressed. Median follow-up of 8.3 months with a median progression-free survival of 6.6 months. Patients who were homozygous A/A or heterozygous A/T genotype at the −251 locus in the IL-8 gene had a lower response rate than those who were T/T (P=0.047 Fisher's exact test). Patients with VEGF(936) C/C had a median time to progression (TTP) of 6.5 months. Patients with any T (T/T, C/T) had a median TTP of 17.2 months. Patients carrying both AM 3'end alleles with fewer than (<)14 3' CA repeats had 3.4 months median TTP; patients with at least one allele having at least (>) 14 CA 3' repeats showed a median TTP of 6.6 months; patients having both alleles with 14 or more (>) 3' CA repeats, showed 8.7 months of median TTP (P=0.0006 Log-rank test).

To the best of Applicant's knowledge, the data shows for the first time that IL-8 (−251) is a potential molecular predictor of response to Bevacizumab based chemotherapy. The data also show that both VEGF 936 and the AM 3' dinucleotide repeat polymorphisms are useful as molecular markers for time to tumor progression (TTP).

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

I claim:

1. A method for determining whether a human ovarian cancer patient is more or less suitably treated by a therapy comprising administration of a bevacizumab antibody or an antibody that binds to the same epitope on VEGF as the bevacizumab, and cyclophosphamide comprising determining the genotype of IL-8 at position −251 present in a nucleic acid sample obtained from the patient, wherein the patient is more suitably treated if the patient's genotype is T/T at position −251 of IL-8 as compared to a patient having a genotype of A/A or A/T at position −251 of IL-8 or the patient is less suitably treated if the patient's genotype is A/A or A/T at position −251 of IL-8 as compared to a patient having a genotype of T/T at position −251 of IL-8.

2. A method for selecting a therapy comprising administration of a bevacizumab antibody or an antibody that binds to the same epitope on VEGF as the bevacizumab antibody, and cyclophosphamide for a human ovarian cancer patient comprising determining the genotype of IL-8 at position −251 present in a nucleic acid sample obtained from the patient wherein the therapy is selected if the patient's genotype is T/T at position −251 of IL-8 or the therapy is not selected if the patient's genotype is A/A or A/T at position −251 of IL-8.

3. A method for treating a human ovarian cancer patient selected for therapy based on presence of a genotype T/T at position −251 of IL-8 comprising administering an effective amount of a therapy comprising a bevacizumab antibody or an antibody that binds to the same epitope on VEGF as the bevacizumab antibody, and cyclophosphamide to the patient, wherein the patient was identified by a method comprising determining the genotype at position −251 of IL-8 present in a nucleic acid sample obtained from the patient.

4. The method of claim 1, wherein the patient is more suitably treated if the patient's genotype is T/T at position −251 of IL-8 as compared to a patient having a genotype of A/A or A/T at position −251 of IL-8.

5. The method of claim 1, wherein the patient is less suitably treated if the patient's genotype is A/A or A/T at position −251 of IL-8 as compared to a patient having a genotype of T/T at position −251 of IL-8.

6. The method of any one of claims 1, 4 and 5, wherein the nucleic acid sample is obtained from at least one of tumor tissue, normal tissue adjacent to the tumor, normal tissue corresponding to the tumor tissue or peripheral blood lymphocytes.

7. The method of claim 2, wherein the therapy is selected if the patient's genotype is T/T at position −251 of IL-8.

8. The method of claim 2, wherein the therapy is not selected if the patient's genotype is A/A or A/T at position −251 of IL-8.

9. The method of any one of claims 2, 7 and 8, wherein the nucleic acid sample is obtained from at least one of tumor tissue, normal tissue adjacent to the tumor, normal tissue corresponding to the tumor tissue or peripheral blood lymphocytes.

10. The method of claim 3, wherein the nucleic acid sample is obtained from at least one of tumor tissue, normal tissue adjacent to the tumor, normal tissue corresponding to the tumor tissue or peripheral blood lymphocytes.

11. The method of claim 1, wherein a patient that is more suitably treated by a therapy is a patient that has a higher response to the therapy.

12. The method of claim 1, wherein a patient that is less suitably treated by a therapy is a patient that has a lower response to the therapy.

13. The method of any one of claims 1, 2, 3, 4, 5, 7, 8 or 10 to 12, wherein the human ovarian cancer patient is a human refractory ovarian cancer patient.

14. The method of any one of claims 1, 2, 3, 4, 5, 7, 8 or 10 to 12, wherein the determining is by a method selected from the group PCR, sequencing, microarray, xMAP, invader assay, mass spectrometry or pyrosequencing.

15. The method of any one of claims 1, 2, 3, 4, 5, 7, 8, or 10 to 12, wherein the therapy comprises administration of a bevacizumab antibody and cyclophosphamide.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acaccatcac catcgacaga                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcggtgattt agcagcaaga                                                   20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttgttctaac acctgccact ct                                                22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcaaacctg agtcatcaca                                                   20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
```

```
                                  -continued aagaggctga gtcagaagga ttgg                                             24

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcaacatcat tttaatatcc tgcacag                                          27
```